US00RE45240E

(19) United States
(12) Reissued Patent
Melder et al.

(10) Patent Number: US RE45,240 E
(45) Date of Reissued Patent: Nov. 11, 2014

(54) PROCESS FOR PREPARING PURE TRIETHANOLAMINE (TEOA)

(71) Applicant: BASF SE, Ludwigshafen (DE)

(72) Inventors: Johann-Peter Melder, Böhl-Iggelheim (DE); Gunther Van Cauwenberge, Lokeren (BE); Tom Fremau, Brasschaat (BE); Jürgen Moors, Kressel-Lo (BE); Thilo Hahn, Kirchheimbolanden (DE); Bernd Stein, Alsbach-Hähnlein (DE)

(73) Assignee: BASF SE (DE)

(21) Appl. No.: 14/085,964

(22) Filed: Nov. 21, 2013

Related U.S. Patent Documents

Reissue of:
(64) Patent No.: 8,466,323
Issued: Jun. 18, 2013
Appl. No.: 13/141,016
PCT Filed: Dec. 10, 2009
PCT No.: PCT/EP2009/066839
§ 371 (c)(1),
(2), (4) Date: Jun. 20, 2011
PCT Pub. No.: WO2010/069856
PCT Pub. Date: Jun. 24, 2010

(30) Foreign Application Priority Data

Dec. 19, 2008 (EP) ..... 08172435

(51) Int. Cl.
*C07C 209/84* (2006.01)
*C07C 209/86* (2006.01)

(52) U.S. Cl.
USPC ..... 564/499

(58) Field of Classification Search
None
See application file for complete search history.

(56) References Cited

U.S. PATENT DOCUMENTS

| | | | | |
|---|---|---|---|---|
| 3,207,790 | A | 9/1965 | Glew et al. | |
| 3,742,059 | A | 6/1973 | Dowd | |
| 3,819,710 | A | 6/1974 | Jordan | |
| 3,849,262 | A * | 11/1974 | Cocuzza | 203/38 |
| 4,673,762 | A | 6/1987 | Paslean et al. | |
| 5,545,757 | A | 8/1996 | Hammer et al. | |
| 6,388,137 | B1 * | 5/2002 | Ruider et al. | 564/499 |
| 6,683,217 | B2 * | 1/2004 | Brun-Buisson et al. | 564/477 |
| 7,279,602 | B2 | 10/2007 | Reif et al. | |
| 7,880,035 | B2 | 2/2011 | Oftring et al. | |
| 7,880,036 | B2 | 2/2011 | Dahmen et al. | |
| 7,915,454 | B2 | 3/2011 | Oftring et al. | |
| 7,960,591 | B2 | 6/2011 | Dahmen et al. | |
| 2006/0293541 | A1 | 12/2006 | Reif et al. | |
| 2010/0016625 | A1 | 1/2010 | Oftring et al. | |
| 2010/0029976 | A1 | 2/2010 | Dahmen et al. | |
| 2010/0029991 | A1 | 2/2010 | Dahmen et al. | |
| 2010/0036168 | A1 | 2/2010 | Ernst et al. | |
| 2010/0056828 | A1 | 3/2010 | Oftring et al. | |
| 2010/0094057 | A1 | 4/2010 | Oftring et al. | |
| 2010/0099872 | A1 | 4/2010 | Dahmen et al. | |
| 2010/0121064 | A1 | 5/2010 | Dahmen et al. | |
| 2010/0121109 | A1 | 5/2010 | Dahmen et al. | |
| 2010/0191000 | A1 | 7/2010 | Melder et al. | |
| 2010/0204438 | A1 | 8/2010 | Cauwenberge et al. | |
| 2010/0240894 | A1 | 9/2010 | Ernst et al. | |
| 2010/0274008 | A1 | 10/2010 | Kubanek et al. | |
| 2010/0274009 | A1 | 10/2010 | Kubanek et al. | |
| 2010/0274011 | A1 | 10/2010 | Kubanek et al. | |
| 2010/0274040 | A1 | 10/2010 | Pai et al. | |
| 2010/0274053 | A1 | 10/2010 | Siegel et al. | |
| 2010/0274054 | A1 | 10/2010 | Staeb et al. | |
| 2010/0274055 | A1 | 10/2010 | Kubanek et al. | |
| 2010/0311973 | A1 | 12/2010 | Ernst et al. | |
| 2011/0009627 | A1 | 1/2011 | Schmidtke et al. | |
| 2011/0033361 | A1 | 2/2011 | Chedid et al. | |
| 2011/0042326 | A1 | 2/2011 | Seeber et al. | |
| 2011/0054167 | A1 | 3/2011 | Kubanek et al. | |
| 2011/0060166 | A1 | 3/2011 | Ernst et al. | |

FOREIGN PATENT DOCUMENTS

| | | | |
|---|---|---|---|
| DE | 2225015 | A1 | 12/1972 |
| EP | 0 004 015 | A1 | 9/1979 |
| EP | 36 152 | A1 | 9/1981 |
| EP | 673 920 | A2 | 9/1995 |
| EP | 1443036 | A1 | 8/2004 |
| GB | 1062730 | A | 3/1967 |
| GB | 1092449 | A | 11/1967 |
| GB | 1453762 | | 10/1976 |
| GB | 1453762 | A | 10/1976 |
| JP | 62005939 | A | 1/1987 |
| JP | 62019558 | A | 1/1987 |
| TW | 424151 | B | 3/2001 |
| TW | 455574 | B | 9/2001 |
| WO | WO-01/53250 | A1 | 7/2001 |
| WO | WO-2005035481 | A2 | 4/2005 |
| WO | WO-2008104579 | A1 | 9/2008 |
| WO | WO-2008129024 | A1 | 10/2008 |
| WO | WO-2008138833 | A1 | 11/2008 |
| WO | WO-2009080515 | A1 | 7/2009 |
| WO | WO-2009127634 | A1 | 10/2009 |
| WO | WO-2009153272 | A2 | 12/2009 |
| WO | WO-2010012672 | A2 | 2/2010 |
| WO | WO-2010/031719 | A1 | 3/2010 |
| WO | WO-2010052181 | A2 | 5/2010 |
| WO | WO-2010054988 | A2 | 5/2010 |
| WO | WO-2010069856 | A1 | 6/2010 |

OTHER PUBLICATIONS

Gu, Y,, et al., "Process for Producing High-Purity Triethanolamine having Excellent Hue", Synthetic Technology and Application, vol. 23, No. 2, (2008), pp. 48-51. (Abstract only).

* cited by examiner

*Primary Examiner* — Brian J Davis
(74) *Attorney, Agent, or Firm* — Drinker Biddle & Reath LLP

(57) ABSTRACT

A process for preparing pure triethanolamine (TEOA) by continuously distillatively separating an ethanolamine mixture comprising TEOA and diethanolamine (DEOA), by distilling off DEOA in a distillation column (DEOA column) and supplying the resulting bottom stream comprising TEOA to a downstream column (TEOA column) in which the pure TEOA is withdrawn as a side draw stream, wherein the residence time of the ethanolamine mixture in the bottom of the DEOA column is <20 minutes.

16 Claims, 1 Drawing Sheet

Drawing for definition of the residence time in a column
Total volume (column bottoms taking account of the bottom level (1) + pipelines (2) + pump (3) + heat exchanger in the bottoms circuit (4))/bottoms effluent (5)
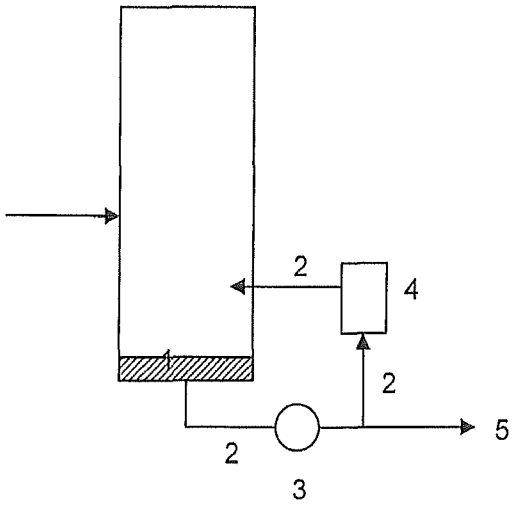

PROCESS FOR PREPARING PURE TRIETHANOLAMINE (TEOA)

Matter enclosed in heavy brackets [ ] appears in the original patent but forms no part of this reissue specification; matter printed in italics indicates the additions made by reissue.

CROSS-REFERENCE TO RELATED APPLICATIONS

This application is a national stage application (under 35 U.S.C. §371) of PCT/EP2009/066839, filed Dec. 10, 2009, which claims benefit of European application 08172435.3, filed Dec. 19, 2008.

BACKGROUND OF THE INVENTION

The invention relates to a process for preparing pure TEOA by continuously distillatively separating an ethanolamine mixture comprising TEOA and diethanolamine (DEOA), by distilling off DEOA in a distillation column (DEOA column) and supplying the resulting bottom stream comprising TEOA to a downstream column (TEOA column) in which the pure TEOA is withdrawn as a side draw stream.

It is common knowledge that an initially colorless, pure TEOA obtained after a fractional distillation of a crude TEOA product which has been obtained by reacting aqueous ammonia with ethylene oxide and distilling off monoethanolamine (MEOA) and diethanolamine (DEOA) (color number: approx. 0 to 20 APHA to DIN-ISO 6271(=Hazen)), after a storage time of approx. 4 to 6 weeks, even in a closed container and with exclusion of light, can gradually turn pale pink and finally, particularly readily when standing under light, yellow to brown. This effect is accelerated by the action of relatively high temperatures (see, for example: G. G. Smirnova et al., J. of Applied Chemistry of the USSR 61, pages 1508-9 (1988), and Chemical & Engineering News 1996, Sep. 16, page 42, middle column).

According to Chemical & Engineering News 1996, Sep. 16, page 42, one mole of TEOA decomposes to one mole of ethanolamine and 2 mol of acetaldehyde at elevated temperature. Acetaldehyde condenses to crotonaldehyde, which in turn forms a Schiff base with ethanolamine. This unsaturated Schiff base leads, with 1,4-polymerization, to colored products in the TEOA.

A method of assessing the color quality of pure TEOA which has been found to be useful, in addition to the time-consuming storage tests in which the APHA color number (to DIN-ISO 6271) of the TEOA is measured as a function of the storage time, is the so-called acid neutralization test.

This acid neutralization test allows the assessment of the color stability in the course of storage of freshly prepared TEOA within a few minutes.

The test is described in Japanese documents JP 62 019 558 A (Derwent abstract No. 87-067647/10) and JP 62 005 939 A (Derwent abstract No. 87-047397/07), according to which the TEOA is treated (neutralized) with acetic acid, citric acid, sulfuric acid, hydrochloric acid or phosphoric acid, and then the absorbance of the absorption bands is measured at 420 nm and 530 nm. When no apparent pink coloration of the TEOA occurs during the performance of the test and the values measured for the absorbance remain sufficiently low, the TEOA is color-stable in the course of storage, i.e. remains colorless over a period of several months, The literature describes various methods of preparing pure and colorless to low-color TEOA.

EP 4015 A (BASF AG) states that ethanolamines with relatively low discoloration are obtained by adding phosphorous acid or hypophosphorous acid during the preparation of the ethanolamines and/or the distillative workup.

EP 36 152 A and EP 4015 A (both BASF AG) explain the influence of the materials used in processes for preparing alkanolamines on the color quality of the process products and recommend nickel-free or low-nickel steels.

U.S. Pat. No. 3,819,710 discloses a process for improving the color quality of ethanolamines by hydrogenating the crude ethanolamines in the presence of selected catalysts. However, the process is technically complex and does not lead to a TEOA product which remains colorless over several months.

U.S. Pat. No. 3,207,790 describes a process for improving the color quality of alkanolamines by adding a borohydride of an alkali metal.

U.S. Pat. No. 3,742,059 and DE 22 25 015 A describe the improvement of the color quality of alkanolamines by the addition of an alkanolamine ester of boric acid or alkali metal/alkaline earth metal borates.

The presence of an assistant to stabilize TEOA is, however, undesired in many important areas of use of the TEOA.

The subsequent addition of small amounts of ethylene oxide to freshly distilled TEOA leads, according to U.S. Pat. No. 4,673,762, likewise to decoloration and color stabilization, However, the method appears to be hazardous for toxicological reasons.

GB 1 062 730 A describes a process for purifying ethanolamines by purifying distillation in the presence of silicates or aluminates.

JP 62 019 558 A (Derwent abstract No. 87-067647/10) reports the preparation of qualitatively good TEOA by treatment of crude TEOA with inorganic oxides at 170 to 250° C. and subsequent distillation in the absence of oxygen.

Similar results are achieved according to JP 62 005 939 A (Derwent abstract No. 87-047397/07) when crude TEOA is heated to 170 to 250° C. with exclusion of air for 1 to 10 h and then distilled under reduced pressure.

SU 326 178 A (Derwent abstract No. 63384T-AE) describes the preparation of TEOA with good color quality by gentle reaction of anhydrous monoethanolamine (MEOA) or diethanolamine (DEOA) or mixtures of the two substances with ethylene oxide at temperatures less than 50° C.

Similar results are achieved according to SU 228 693 A (Chem. Abstr. 70, 77305f (1969)) and GB 1 092 449 A when ammonia is reacted with ethylene oxide at less than/equal to 35° C. and the resulting ethanol amine mixture is distilled with exclusion of air.

From an economic point of view, those processes in which the reactions with ethylene oxide take place at low temperatures are inefficient owing to the long residence times and the associated low space-time yields.

WO 2001/53250 A1 (BP Chemicals Ltd.) relates to a continuous process for the manufacture of TEOA comprising (i) a step of synthesizing the TEOA by continuously bringing ammonia into contact with ethylene oxide, under conditions allowing the formation of a reaction mixture comprising mono-, di- and triethanolamines, (ii) a step of continuously separating the ammonia that has not reacted from the reaction mixture, and (iii) a step of continuously separating the TEOA from the mixture resulting from step (ii), which process is characterized in that, in the last step, the monoethanelamine and some of the diethanolamine are separated from the mixture resulting from step (ii), a specific mixture of alkanolamines comprising TEOA and from 0.5 to 50% by weight of at least one secondary dialkanolamine is prepared or isolated, and in that the TEOA is separated and isolated with a degree of purity of ≥99.2% by weight by continuous distillation of the specific mixture of alkanolamines.

WO 2005/035481 A2 (BASF AG) describes the distillative removal of triethanolamine, in which the substance mixture is distilled in two stages. In the first stage, the low boiler fraction and the high boiler fraction are withdrawn and discharged, and, in the second stage, the medium boiler fraction with a triethanolamine content of >99.4% by weight and a diethanolamine content of <0.2% by weight is distilled. The substance mixture is distilled preferably in a first column and a second column connected thereto, or in a dividing wall column.

BRIEF SUMMARY OF THE INVENTION

It was an object of the present invention, overcoming disadvantages of the prior art, to provide an improved process for preparing triethanolamine by removing triethanolamine from a substance mixture obtained especially by the reaction of ammonia with ethylene oxide. For the TEOA, a high purity and color quality, i.e. reduction of discoloration and/or improvement in color stability, especially in the course of storage, should be achieved. The preparation process should additionally be particularly simple and economically viable.

Accordingly, a process has been found for preparing pure triethanolamine (TEOA) by continuously distillatively separating an ethanolamine mixture comprising TEOA and diethanolamine (DEOA), by distilling off DEOA in a distillation column (DEOA column) and supplying the resulting bottom stream comprising TEOA to a downstream column (TEOA column) in which the pure TEOA is withdrawn as a side draw stream, wherein the residence time of the ethanolamine mixture in the bottom of the DEOA column is <20 minutes.

The invention is based on the recognition that the color quality, i.e. reduction of discoloration and/or improvement in color stability, especially in the course of storage, of the triethanolamine can be influenced positively by reducing the residence time of the ethanolamine mixture comprising di- and triethanolamine in the column bottom during the removal of the diethanolamine from this mixture.

BRIEF DESCRIPTION OF THE FIGURE

FIG. 1 demonstrates the defnition of the residence time in a column.

DETAILED DESCRIPTION OF THE INVENTION

The invention preferably uses a substance mixture which is obtained as follows. First, for example according to EP 673 920 A (BASF AG), by the reaction of aqueous ammonia with ethylene oxide in the liquid phase under elevated pressure and elevated temperature in a suitable reactor, an ethanolamine mixture is prepared, comprising the main components monoethanolamine (MEOA), diethanolamine (DEOA) and triethanolamine (TEOA).

The reaction temperatures here are especially 110 to 180° C., preferably 120 to 150° C., and the pressures are especially 50 to 150 bar (5 to 15 MPa), preferably 75 to 120 bar (7.5 to 12 MPa). The molar ratio of ammonia to ethylene oxide is especially 1:1 to 100:1, preferably 3:1 to 50:1, more preferably 4:1 to 15:1, and the ammonia is used particularly as a 60 to 99.99% by weight, preferably 70 to 95% by weight, aqueous solution. The ethylene oxide used can be added as the entire amount at once or in 2 to 10, preferably 2 to 6, portions of in each case 1 to 99% by weight, preferably 5 to 95% by weight, for example 10 to 70% by weight (based in each case on the total amount of EO).

When a molar ratio of ammonia to ethylene oxide of more than 1:1 is employed, the excess ammonia is subsequently distilled out of the resulting product mixture in a manner known per se together with a portion of the water under elevated pressure (i.e. >1 bar (abs.)), and then the residual water is distilled off, preferably at standard pressure or lower. What remains is a crude product which comprises essentially MEOA, DEOA and TEOA with a water content of preferably less than 0.3% by weight, more preferably less than 0.1% by weight.

After the subsequent distillative removal of the monoethanolamine (MEOA) in an MEOA column at an absolute pressure of <1 bar, what remains is a crude product consisting of DEOA, TEOA and small amounts of secondary components, for example (2-(2-hydroxyethoxy)ethyl)di(2-hydroxyethyl) amine, (2-(2-hydroxyethoxy)ethyl)-(2-hydroxyethypamine and N,N'-di(2-hydroxyethyl)piperazine. A typical crude mixture comprises, for example, 50 to 80% by weight of DEOA and 20 to 50% by weight of TEOA.

The residence time of the ethanolamine mixture in the bottom of the MEOA column is preferably <35 minutes, for example in the range from 3 to 30 min, preferably <15 minutes, for example in the range from 2 to 10 min, more preferably <7 minutes, for example in the range from 1 to 5 min.

For the definition of the residence time in the bottom of the MEOA column, the same applies here as for the definition of the residence time in the bottom of the DEOA column specified below. The MEOA column is adjusted so as to result in a reflux ratio in the range from especially 0 to 0.9, preferably from 0.1 to 0.4.

The composition of this crude product may vary according to the originally used molar ratio of ammonia to ethylene oxide.

In general, the resulting ethanolamine mixture comprising predominantly DEOA and TEOA can be subjected directly to a fractional distillation, in which pure DEOA and TEOA are obtained in succession.

However, an alternative procedure is possible, in which this crude product comprising predominantly DEOA and TEOA, which has a water content of preferably less than 0.3% by weight, especially less than 0.1% by weight, and an ammonia content of preferably less than 0.1% by weight, especially less than 0.01% by weight, is reacted with 0.6 to 1.2 mol, preferably 0.8 to 1.1 mol, of ethylene oxide (EO) per gram atom of hydrogen bonded to nitrogen in the crude product at temperatures of 110 to 180° C., preferably 120 to 180° C., in the liquid phase. This reaction is effected especially as described in GB 1 453 762 A. Preference is given to effecting the reaction in tubular reactors and in several stages, in which case, for example, 50 to 80% by weight of the ethylene oxide used is converted in a first reaction stage at temperatures of preferably 125 to 165° C., the remaining amount of the ethylene oxide used is converted in a second reaction stage at temperatures of preferably 150 to 180° C., and the reaction is conducted to completion in a third reaction stage at temperatures of 120 to 150° C. The ethanolamine mixture comprising DEOA and TEOA, preferably comprising predominantly DEOA and TEOA, used in the process according to the invention more preferably has DEOA and TEOA contents as follows:

DEOA: 50 to 80% by weight, especially 60 to 75% by weight.
TEOA: 20 to 50% by weight, especially 25 to 40% by weight.

According to the invention, the ethanolamine mixture comprising DEOA and TEOA is continuously separated by distillation. Suitable apparatus for this purpose is customary distillation apparatus. Such apparatus is known to a person skilled in the art.

To remove a predominant amount of DEOA from the mixture, a DEOA column is used. To remove the TEOA from the resulting mixture comprising DEOA residues, a downstream TEOA column is used. It is possible with preference to use distillation columns with at least one transverse or longitudinal division, embodied in the form of a tray, of a dividing wall, of structureD packings or of random packings, as described, for example, in WO 2005/035481 A2 (BASF AG).

The so-called DEOA column, in which the diethanolamine is first separated from the triethanolamine, is operated at a temperature in the bottom in the range from preferably 170° C. to 200° C. The absolute pressure selected varies preferably at values in the range from 10 mbar to 20 mbar.

Pressure data for distillation columns in this document are always based on the absolute pressure in the top of the column.

The column is adjusted so as to result in a reflux ratio in the range of especially 0 to 0.6, preferably of 0.25 to 0.4.

Definition of 'reflux ratio': mass ratio of condensate recycled into the column and drawn off as distillate at the top of a distillation column.

The ethanolamine mixture comprising DEOA and TEOA is preferably fed into the DEOA column at the side, particularly into the side of the middle column region.

According to the invention, the residence time of the ethanolamine mixture in the bottom of the DEOA column is <20 minutes, for example in the range from 1 to 18 min, preferably <15 minutes, for example in the range from 2 to 13 min, more preferably <12 minutes, for example in the range from 3 to 11 min.

The residence time in the bottom of the DEOA column is understood to mean the time which is calculated when the actual liquid volumes of column bottom, pipelines and pump in the bottoms circuit and holdup in the evaporator/heat exchanger are added up and divided by the volume flow which is withdrawn from this bottoms circuit. The drawing of FIG. 1 serves for further explanation on this subject.

The diethanolamine is isolated from the DEOA column preferably as a side draw stream and preferably has a purity of z 99.3% by weight.

The bottoms of the DEOA column, which are conducted to the downstream TEOA column, comprise particularly in the range from 15 to 33% by weight of DEOA, 65 to 83% by weight of TEOA and 0.1 to 2% by weight of other secondary components.

The TEOA column in which the triethanolamine is isolated is operated at a temperature in the bottom of preferably in the range from 170° C. to 200° C. The absolute pressure selected varies preferably from values of 1 mbar to 10 mbar.

The column is adjusted so as to result in a reflux ratio in the range from especially 0 to 0.6, preferably from 0.1 to 0.4.

The ethanolamine mixture comprising DEOA and TEOA for separation is preferably fed into the TEOA column at the side, particularly into the side of the middle column region.

A low boiler fraction comprising a mixture of diethanolamine (60 to 100% by weight, particularly 70 to 95% by weight) and triethanolamine (0 to 40% by weight, particularly 5 to 30% by weight) is removed at the top of the column and, if appropriate, fed back into the DEOA column.

The high boiler fraction consists of triethanolamine (50 to 100% by weight, particularly 80 to 98% by weight, of TEOA) and secondary components, and is withdrawn and discharged at the bottom of the column.

The remaining medium boiler fraction with a triethanolamine content of ≥99.3% by weight, particularly ≥99.4% by weight, is isolated as a side draw stream, preferably in the middle portion of the TEOA column.

Owing to the thermal sensitivity of the ethanolamine mixture, it is advantageous to operate the TEOA column with an evaporator which has a low wall temperature and a small liquid capacity. Overall, it has been found to be particularly favorable to use a falling film evaporator. The column bottom and the evaporator bottom are configured such that the residence time of the high boiler fraction in the bottom of the TEOA column is in the range from 10 to 180 min, preferably 30 to 150 min. At these residence times, an optimum of the removal of the medium boiler fraction and the prevention of formation of undesired by-products is achieved.

For the definition of the residence time in the bottom of the TEOA column, the same applies here as for the above-specified definition of the residence time in the bottom of the DEOA column.

In an advantageous embodiment, the TEOA obtained in the side draw in the TEOA column, for further purification and/or improvement in the color quality, is distilled in a further downstream column and removed there via the top, especially as described in WO 2005/035481 A2 (BASF AG). The high boilers obtained in the bottom of the downstream column are preferably recycled into the middle region of the TEOA column. The reflux ratio in the downstream column is preferably in the range from 0.2 to 0.7. The TEOA column and the downstream column are preferably operated with equal or approximately equal temperature profiles.

In a further advantageous embodiment, the TEOA column is a dividing wall column, especially as described in WO 2005/035481 A2 (BASF AG). A dividing wall column is in principle an apparatus simplification of two thermally coupled distillation columns. It generally comprises a vertical dividing wall which extends above and below the feed point, which divides the column into a feed section and a withdrawal section. The dividing wall column may be configured as a packed column comprising random packings or structured packings, or as a tray column. The substance mixture is fed into the column in the middle region of the dividing wall. The first distillation stage is carried out in the feed section of the column, and the medium boiler fraction which remains after withdrawal of the low boiler fraction at the top of the column and high boiler fraction at the bottom of the column is distilled in the withdrawal section of the column, pure triethanolamine (TEOA) being discharged via a side draw in the middle region of the dividing wall (opposite the introduction point), and the high boilers which form in the second distillation stage likewise being discharged in the bottom of the column.

In further embodiments, a plurality of DEOA columns and TEOA columns (in each case, for example, 2 or 3) can be operated and connected as desired. The discharge from the DEOA column can either be conducted directly into the TEOA column or else stored intermediately first.

The process according to the invention affords TEOA particularly in a purity of ≥99.3% by weight, more particularly ≥99.4% by weight, especially ≥99.8% by weight.

The APHA color number of TEOA obtained in accordance with the invention is particularly ≤100, more particularly ≤90, and is very particularly in the range from 30 to 80.

TEOA in particularly good color quality, particularly with an APHA color number of ≤20, and high color stability is obtained when, as described especially in EP 4015 A and EP 1 132 371 A, an effective amount of phosphorous acid or hypophosphorous acid or a derivative of one of these acids (e.g. a salt, e.g. sodium salt) is added before or during the ethanolamine synthesis from ethylene oxide and ammonia and/or in the course of the distillative separation of the resulting ethanolamine mixture. It is preferably not added until before the TEOA purifying distillation in the TEOA column. When the additive is added after the reaction of ethylene oxide and ammonia in the distillation of the ethanolamines obtained therefrom, the amount metered in is preferably in the range from 0.005 to 2% by weight based on the sum of the ethanolamines (MEOA, DEOA, TEOA), in the feed to the column in question.

The APHA color number of TEOA obtained in accordance with the invention in this way is particularly ≤20, more particularly ≤15, and is very particularly in the range from 1 to 10.

EXAMPLES

The APHA color number is determined to DIN-ISO 6271.

Example 1a

An ethanolamine mixture comprising the main components monoethanolamine (MEOA), diethanolamine (DEOA) and triethanolamine (TEOA) was prepared by the reaction of aqueous ammonia with ethylene oxide in the liquid phase under elevated pressure and elevated temperature in a suitable reactor. After removal of $NH_3$, water and MEOA, the resulting ethanolamine mixture was conducted into a DEOA column in order to isolate DEOA. The feed to the DEOA column comprised 1.6% by weight of MEOA, 70.2% by weight of DEOA and 28.2% by weight of TEOA. The DEOA column was operated at an absolute pressure of 14 mbar and with a top temperature of 135° C. and with a bottom temperature of 189° C.; the reflux ratio was 0.33.

The residence time of the mixture in the bottom of the DEOA column was set to 18 minutes.

The top product obtained was DEOA with a purity of 99.5% by weight.

The bottom product (23% by weight of DEOA, 76% by weight of TEOA, 1% by weight of secondary components) was then conducted into the TEOA column which was operated at an absolute pressure of 1.3 mbar and with a top temperature of 71° C. and with a bottom temperature of 185° C. The reflux ratio was 0.22.

In the feed to the TEOA column, phosphorous acid (0.12% by weight based on the feed to the column) was added. The top product of the TEOA column was recycled into the DEOA column. The side effluent was conducted into a further downstream column. At the top of the downstream column, TEOA was isolated with a purity of 99.52% by weight and a color number of 20 APHA.

Example 1b

Under the same conditions as described above but with a reduced residence time of the mixture in the bottom of the DEOA column of 7 minutes, TEOA was obtained with a purity of 99.62% by weight and a color number of 6 APHA.

The residence time was in each case calculated as described above.

The examples show that reduction of the residence time of the bottoms mixture in the DEOA column and hence a reduction in the thermal stress on the TEOA during the removal of the different ethanolamines achieves a positive effect on the color quality, especially the color number, of the triethanolamine. When the residence time in the bottom of the DEOA column is reduced, especially to <20 minutes, more preferably <12 minutes, a significantly less colored triethanolamine is obtained.

Example 2

The following example illustrates that a long thermal stress on an ethanolamine mixture from the column bottom of the DEOA column, as occurs as a result of an increased residence time in the column bottom, leads to the loss of product of value and a significant rise in the color number. This significantly complicates the purification of TEOA in the downstream column.

The bottom product of a DEOA column was analyzed: 17.0% by weight of DEOA, 81.4% by weight of TEOA, 1.6% by weight of secondary components, color number (APHA) 17. This mixture was heated at 190° C. under nitrogen for 1 h. The proportion of secondary components rose to 4.0% by weight and the color number (APHA) increased to 120.

Example 3

A TEOA column with a side draw column according to WO 2005/035481 A was charged with a mixture of DEOA, TEOA and secondary components according to the list below (feed 1 and 2). These feeds were bottom products of a DEOA distillation which had been obtained at different residence times in the bottom of the DEOA column. The residence time was in each case calculated as described above.

Feed 1: 24% by weight of DEOA, 72% by weight of TEOA, 4% by weight of secondary components, obtained from a DEOA distillation at approx. 180° C. with residence time >30 min and <70 min in the bottom of the column. Feed 2: 17% by weight of DEOA, 79% by weight of TEOA, 4% by weight of secondary components, obtained from a DEOA distillation at bottom temperature 175 to 180° C. with residence time 5 to 10 min in the bottom of the column.

The TEOA column was operated at top pressure 4 mbar (abs.), bottom temperature 195° C., top temperature 160° C. and a reflux ratio at the top of the column (reflux ratio here only defined as follows: amount of reflux (liters)/total amount of top effluent (liters)) of 0.1 with metered addition of 0.05% by weight of phosphorous acid (based on the column feed). TEOA was isolated in the top of a downstream column (side draw column).

With feed 1, TEOA was obtained with a purity of 98.7% by weight and a color number (APHA) of 17.

With feed 2, TEOA was obtained with a purity of 99.4% by weight and a color number (APHA) of 3.

The example shows: a long residence time in the bottom of the DEOA column has an adverse effect on the downstream TEOA distillation, and leads to a TEOA quality with lower purity and worse color number.

The invention claimed is:

1. A process for preparing pure triethanolamine (TEOA) by continuously distillatively separating an ethanolamine mixture comprising TEOA and diethanolamine (DEOA), comprising distilling off DEOA in a distillation column (DEOA column) and supplying the resulting bottom stream comprising TEOA to a downstream column (TEOA column) in which the pure TEOA is withdrawn as a side draw stream, wherein the residence time of the ethanolamine mixture in the bottom of the DEOA column is <20 minutes.

2. The process according to claim 1, wherein the residence time of the ethanolamine mixture in the bottom of the DEOA column is <15 minutes.

3. The process according to claim 1, wherein the residence time of the ethanolamine mixture in the bottom of the DEOA column is in the range from 3 to <12 minutes.

4. The process according to claim 1, wherein the DEOA is withdrawn in the DEOA column as a side draw stream.

5. The process according to claim 1, wherein the DEOA is withdrawn in a purity of ≥99.3% by weight.

6. The process according to claim 1, wherein the TEOA of the TEOA column is withdrawn in a purity of ≥99.3% by weight.

7. The process according to claim 1, wherein a product stream comprising ≥60% by weight of DEOA and ≤40% by weight of TEOA is withdrawn at the top of the TEOA column.

8. The process according to claim 1, wherein the product stream withdrawn at the top of the TEOA column is recycled into the DEOA column.

9. The process according to an claim 1, wherein the TEOA obtained in the side draw in the TEOA column is distilled in a further downstream column and removed there via the top.

10. The process according to claim 1, wherein the TEOA column is a dividing wall column.

11. The process according to claim 1, wherein the ethanolamine mixture comprising TEOA and DEOA for separation has been obtained beforehand by reacting ammonia with ethylene oxide in the liquid phase and subsequently removing $NH_3$, water and monoethanolamine (MEOA).

12. The process according to claim 1, wherein phosphorous acid or hypophosphorous acid or a derivative of one of these acids is added to the ethanolamine mixture for separation.

13. The process according to claim 1 wherein the pure TEOA has an APHA color number of ≤20.

*14. The process according to claim 1, wherein the DEOA column is operated at a temperature in the bottom in the range from 170° C. to 200° C.*

*15. The process according to claim 1, wherein the ethanolamine mixture comprising TEOA and DEOA is fed into the side of the DEOA column.*

*16. The process according to claim 1, wherein the TEOA column is operated at a temperature in the bottom on the range from 170° C. to 200° C.*

* * * * *